United States Patent [19]

Fernholz et al.

[11] 3,997,598

[45] Dec. 14, 1976

[54] PROCESS FOR PURIFYING SORBIC ACID

[75] Inventors: Hans Fernholz, Fischbach, Taunus; Hans-Joachim Schmidt, Falkenstein, Taunus; Friedrich Wunder, Florsheim, Main, all of Germany

[73] Assignee: Hoechst Aktiengesellschaft, Frankfurt am Main, Germany

[22] Filed: June 20, 1974

[21] Appl. No.: 481,461

[30] Foreign Application Priority Data

June 22, 1973 Germany ............................ 2331668

[52] U.S. Cl. ........................................... 260/526 N
[51] Int. Cl.[2] .......................................... C07C 51/42
[58] Field of Search ................................ 260/526 N

[56] References Cited

UNITED STATES PATENTS 3,759,988  9/1973  Kunstle et al. ................ 260/526 N

FOREIGN PATENTS OR APPLICATIONS 917,225  1/1963  United Kingdom ........... 260/526 N Primary Examiner—Vivian Garner
Attorney, Agent, or Firm—Curtis, Morris & Safford

[57] ABSTRACT

Process for purifying sorbic acid by recrystallization from aqueous solutions of an alkali metal or ammonium salt of a carboxylic acid or phosphoric acid. Impurities may be eliminated in addition by means of an adsorption agent.

21 Claims, No Drawings

PROCESS FOR PURIFYING SORBIC ACID

It is known that sorbic acid is substantially used as preservative for foodstuffs. For this reason, the purification of the crude acid prepared by various methods and having a different degree of purity is especially important. Several processes for purifying have been described up till now. Crude sorbic acid may be purified, for example by distillation with an entrainer, which can be distilled without decomposition, has a boiling point of from 180° to 300° C and is inert towards sorbic acid. This process leads to a very pure sorbic acid. A disadvantage thereof is however the additional energy consumption necessary for evaporating the entrainer and the relatively high technical expenditure, especially when simultaneously working at low pressure.

Further processes for purifying based on the volatility in steam of sorbic acid are uneconomic because of the high consumption of steam.

In other processes organic solvents are used in order to recrystallize or purify by adsorption the sorbic acid. In general they are likely to result in an acid which does not comply with the regulations governing the purity of sorbic acid.

Finally are known a series of processes using water as solvent and purifying sorbic acid by extraction, flotation or recrystallization. These methods have not become industrially important owing to the low solubility of sorbic acid in water, inter alia.

It has now surprisingly been found that the solubility of sorbic acid in water, which is approximately 3 % at 100° C, can be materially improved by adding an alkali metal salt or ammonium salt easily soluble in water of a carboxylic acid only containing carbon, hydrogen and oxygen atoms and having one carboxylic group or of a phosphoric acid in an amount of at least 15 % by weight, calculated on the quantity of water used, or by using as solvent an aqueous solution of the aforesaid salt. In this process the solubility of the sorbic acid is directly proportional to the concentration of the salt solution. When using solutions containing of 30 % by weight of the aforesaid salt, at room temperature (20° C) or at a temperature of 80° C, the following solubility values are obtained for sorbic acid (grams per 100 ml of a salt solution):

a crude sorbic acid contaminated to a higher degree an additional treatment with an adsorption agent is required, in general.

The present invention consequently provides a process for purifying sorbic acid, which comprises recrystallisation of the crude sorbic acid from an aqueous solution containing of at least 15 % by weight of an alkali metal or ammonium salt of a carboxylic acid, containing only carbon, hydrogen and oxygen atoms and having one carboxylic group, or of a phosphoric acid.

As alkali metal salts sodium and potassium salts are used, in general. Preferred carboxylic acids are those having a dissociation constant of from pK 3.8 to 5.0. Example of those salts can be seen from the above table. Using sodium, potassium or ammonium acetates may be advantageous for economic reasons. Naturally the upper limit of the concentration of the aqueous salt solution is defined by the solubility in water of the alkali metal or ammonium salt. In general it is advantageous to use 20 to 35 % weight salt solutions.

The process according to the invention can be carried out in quite simple manner. In general the crude sorbic acid is dissolved in an aqueous salt solution at temperatures ranging from 50° to 100° C. Impurities remaining undissolved in this process may be separated in usual manner by filtration or centrifugation of the solution while still hot. If the crude sorbic acid is contaminated to a higher degree an additional treatment of the hot solutions with an adsorption agent is advantageous. As adsorption agents there may be mentioned the usual porous and surface-active agents, such as active carbon, bone charcoal, diatomaceous earth, bauxite, bentonite or adsorption resins. A surface-active carbon derived from mineral coal is preferably used. The treatment of the hot crude sorbic acid solution with an adsorption agent, as for example active carbon derived from mineral coal can be carried out discontinuously or continuously.

In the former case the active carbon is advantageously suspended in finely divided form in the aqueous solution of the sorbic acid while still hot and kept in motion by stirring or shaking. For continuous operation it is recommended to use a granular active carbon. In this process the carbon may be contained in a column or a system of series connected columns or towers of suitable design in either a stationary or mobile state, for

| salt | solubility at a temperature of 20° C | 80° C |
| --- | --- | --- |
| 1. sodium acetate | 2.0 | 30.0 |
| 2. potassium acetate | 1.8 | 29.0 |
| 3. ammonium acetate | 2.2 | 31.0 |
| 4. sodium propionate | 3.9 | 39.5 |
| 5. sodium ethyl capronate | 8.8 | 37.6 |
| 6. potassium sorbate | 0.8 | 20.7 |
| 7. sodium benzoate | 4.7 | 32.0 |
| 8. sodium salicylate | 1.9 | 13.6 |
| 9. sodium-p-hydroxybenzoate | 3.2 | 23.5 |
| 10. dipotassium hydrogen phosphate | 7.9 | 15.1 |

From this table can be seen that aqueous salt solutions are distinguished by a high dissolving power at elevated temperatures and by a relatively low dissolving power at room temperature. Consequently they are especially suitable for purifying sorbic acid by recrystallization. The degree of purity of the crude sorbic acid is, of course, decisive for this process. When using example as sliding bed through which the sorbic acid solution is passed in an upward or downward direction and in a parallel or counter-current flow. The continuous operation is preferred for purifying sorbic acid on an industrial scale. In this case it is advantageous to substantially exclude oxygen by superposing an inert gas, as for example nitrogen.

The pure sorbic acid crystallizes from the solution — which is optionally purified — while cooling. In this process, the particle size of the sorbic acids crystals essentially depends on the speed of cooling and stirring. In the case of a very slow stirring and cooling the main part of the crystallized product consists of sorbic acid crystals having a particle size of more than 500 $\mu$. In the case of a quick stirring and cooling, however, mainly sorbic acid crystals having a particle size of less than 200 $\mu$ are obtained. A great advantage of the process according to the invention is that a controlled crystallization can be carried out, which is of great importance for preparing sorbic acid free or almost free from dust.

As the aqueous alkali metal or ammonium salt solution can be reused as solvent practically without any limit after adsorptive purification and after separation of the crystallized sorbic acid, the process according to the invention is very economically.

The process according to the invention has the further advantage that an extremely pure and stable alkali metal salt sorbate is obtained by neutralizing with sodium hydroxide or potassium hydroxide solution the sorbic acid purified according to the invention.

The following examples illustrate the invention.

EXAMPLE 1

190 g of a sorbic acid (content: 98.2 %) having a light-yellow colour are dissolved in 1 l of an aqueous solution containing 30 % by weight of potassium sorbate at 80° C. After cooling to room temperature the crystallized product is filtered off, washed with 200 ml of water and dried. 178 g of colourless sorbic acid are obtained (content: 99.8 %) having a melting point of 134° C. By reusing the potassium sorbate solution, obtained as filtrate, 186 g of a colourless sorbic acid (melting point 134° C, content: 99.7 %) are obtained from 190 g of the sorbic acid having a content of 98.2 %.

EXAMPLE 2

250 g of the sorbic acid of example 1 (content 98.2 %) are dissolved in 1 l of an aqueous solution containing 30 % by weight of sodium acetate, at a temperature from 70° to 80° C. After cooling to room temperature the crystallized product is drawn off, washed with 300 ml of water and dried. 225 g of colourless sorbic acid (content: 99.7 %, melting point 134° C) are obtained.

EXAMPLE 3

260 g of the same sorbic acid as in example 1 (content 98.2 %) are dissolved in 1 l of an aqueous solution containing 30 % by weight of ammonium acetate at a temperature of 70° C. After cooling to room temperature the crystallized product is filtered off, washed with 250 ml of water and dried. 233 g of colourless sorbic acid (content: 99.8 %, melting point 134° C) are obtained.

EXAMPLE 4

350 g of the sorbic acid of example 1 (content 98.2 %) are dissolved in 1 l of an aqueous solution containing 30 % by weight of sodium propionate at a temperature of 80° C.

After cooling to room temperature the crystallized product is filtered off, washed with 300 ml of water and dried. 305 g of colourless sorbic acid (content: 99.6 %, melting point 133° to 134° C) are obtained.

EXAMPLE 5

200 g of the sorbic acid of example 1 (content 98.2 %) are dissolved in 1 l of an aqueous solution containing 30 % by weight of sodium-p-hydroxybenzoate at a temperature of from 70° to 80° C. After cooling to room temperature the crystallized product is filtered off, washed with 200 ml of water and dried. 164 g of colourless sorbic acid (content: 99.9 %, melting point 134° C) are obtained.

EXAMPLE 6

150 g of the sorbic acid of example 1 (content 98.2 %) are dissolved in 1l of an aqueous solution containing 30 % by weight of dipotassium hydrogen phosphate at a temperature of 80° C. After cooling to room temperature the crystallized product is filtered off, washed with 250 ml of water and dried. 68 g of colourless sorbic acid (content: 99.8 %, melting point 134° C) are obtained. By reusing the phosphate solution obtained as filtrate, the sorbic acid yield is quantitative.

EXAMPLE 7

200 g of a sorbic acid contaminated by polymers during the preparation process (content: 94.6 %) are dissolved in 1 l of an aqueous solution containing of 30 % by weight of sodium acetate at a temperature of from 80° to 90° C, stirred under nitrogen atmosphere for a period of 1 hour on addition of 50 g of highly active bleaching earth and filtered while still hot. After cooling to room temperature the crystallized product is washed with 200 ml of water and dried. 168 g of colourless sorbic acid (content: 99.4 %, melting point 133° to 134° C) are obtained.

EXAMPLE 8

200 g of the same sorbic acid as in example 7 are dissolved in 1 l of an aqueous solution containing of 30 % by weight of sodium acetate at a temperature of 80° C, stirred for 1 hour under nitrogen atmosphere on addition of 20 g of active carbon and filtered while still hot. After cooling to room temperature the crystallized product is washed with 100 ml of water and dried. 169 g of colourless sorbic acid (content: 99.8 %, melting point 134° C) are obtained.

EXAMPLE 9

200 g of the same sorbic acid as in example 7 are dissolved in 1 l of an aqueous solution containing of 30 % by weight of sodium acetate at a temperature of 80° C. 10 g of active carbon (basis: mineral coal) are added, the whole is stirred for a period of 30 minutes and filtered while still hot. After cooling to room temperature the crystallized product is washed with 150 ml of water and dried. 168 g of colourless sorbic acid (content: 99.9 %, melting point 134° C) are obtained.

EXAMPLE 10

A tube having a length of 10 m and a diameter of 4 cm and being provided with a heating coat is filled so as to be free from gas bubbles with active carbon (basis: mineral coal, particle size: 2 to 4 mm) impregnated with a 30 % by weight aqueous sodium acetate solution. A solution of 20 parts by weight of a crude sorbic acid having a brown colour in 10 parts by weight of an aqueous 30 % by weight sodium acetate solution is pumped in an upward direction through this column under nitrogen atmosphere at a rate of 1 l per hour, at a temperature of from 70° to 80° C. The purified solution is filtered while still hot. After cooling to room temperature the crystallized product is washed with water and dried as described in example 2. At the beginning 144 to 145 g of colourless sorbic acid are obtained having a melting point of 134° C (content: 99.8 %). By reusing the acetate solution obtained as filtrate and saturated with sorbic acid of from 164 to 165 g of sorbic acid are obtained per hour having the same degree of purity.

EXAMPLE 11

A tube having a length of 10 m, a diameter of 8 cm and being provided with a heating coat is continuously filled at the top with the active carbon described in example 10, while the corresponding quantity of used carbon is drawn off at the bottom of the column. The crude sorbic acid solution described in example 10 is pumped through this sliding carbon bed in a countercurrent flow under nitrogen atmosphere at a temperature of from 70° to 80° C, having a residence time of 5 hours. The purified sorbic acid solution is filtered while still hot and the pure sorbic acid is obtained as described in example 10. When equilibrium has been reached, 0.5 kg of active carbon are required for purifying 15 kg of sorbic acid.

What is claimed is:

1. A process for purifying sorbic acid which comprises dissolving crude sorbic acid in an aqueous solution, at an elevated temperature in the range of 50° to 100° C, said solution containing at least 15 percent by weight of a water soluble alkali metal or ammonium salt of a monocarboxylic acid having only carbon, hydrogen and oxygen atoms or a phosphoric acid, and subsequently cooling and crystallizing pure sorbic acid from said solution and separating the crystallized sorbic acid from the solution.

2. Process as claimed in claim 1 wherein impurities in the sorbic acid solution are removed additionally by contacting said solution at said elevated temperatures with an adsorption agent.

3. Process as claimed in claim 2, wherein an active coal derived from mineral coal is used as the absorption agent.

4. Process as claimed in claim 1, wherein an aqueous solution of the sodium or potassium salt of a carboxylic acid having a dissociation constant of from pK 3.8 to 5.0 is used.

5. Process as claimed in claim 1, wherein 20 to 35 % by weight solutions of the alkali metal or ammonium salt are used.

6. The process of claim 1 wherein the salt is a member selected from the group consisting of monocarboxylic acid salts.

7. The process of claim 1 wherein the salt is a member selected from the group consisting of phosphoric acid salts.

8. The process of claim 1 wherein the aqueous solution at said elevated temperature, containing the dissolved sorbic acid and impurities is contacted with an adsorbent bed, said adsorbent bed removing impurities from the solution and the aqueous solution is separated from the adsorbent bed.

9. The process for purifying sorbic acid which comprises dissolving crude sorbic acid in an aqueous solution, at an elevated temperature in the range of 50°–100° C., said solution comprising at least 15 percent by weight of a salt which is a member selected from the group consisting of sodium acetate, potassium acetate, ammonium acetate, sodium propionate, sodium ethyl capronate, potassium sorbate, sodium benzoate, sodium salicylate, sodium-p-hydroxybenzoate and dipotassium hydrogen phosphate, cooling and crystallizing pure sorbic acid from said solution and separating the crystallized sorbic acid from the solution.

10. The process of claim 9 wherein additional impurities are removed by passing the solution at said elevated temperature through an adsorbent bed.

11. The process of claim 10 wherein the adsorbent bed comprises an adsorbent which is a member selected from the group consisting of active carbon, bone charcoal, diatomaceous earth, bauxite, bentonite and adsorption resin.

12. The process of claim 9 wherein the salt comprises 20 to 35 percent by weight of the solution, the solution is cooled at ambient temperature to crystallize sorbic acid and the crystallized sorbic acid is separated from the solution.

13. A process for purifying sorbic acid which comprises dissolving crude sorbic acid in an aqueous solution at a temperature of 50° to 100° C, said solution comprising 20 to 35% by weight of a salt which is a member selected from the group consisting of sodium acetate, potassium acetate, ammonium acetate, sodium propionate, sodium ethyl capronate, potassium sorbate, sodium benzoate, sodium salicylate and sodium-p-hydroxybenzoate, separating insoluble impurities, cooling and crystallizing pure sorbic acid from said solution and separating the crystallized sorbic acid from the solution.

14. The process of claim 13 wherein insoluble impurities are separated from the heated solution and the solution is cooled to ambient temperature to crystallize sorbic acid and the crystallized sorbic acid is separated therefrom.

15. The process of claim 13 wherein the crude sorbic acid has a light yellow color and the aqueous solution comprises potassium sorbate.

16. The process of claim 13 wherein the aqueous solution comprises sodium acetate.

17. The process of claim 13 wherein the aqueous solution comprises ammonium acetate.

18. The process of claim 13 wherein the aqueous solution comprises sodium propionate.

19. The process of claim 13 wherein the aqueous solution comprises sodium-p-hydroxybenzoate.

20. The process of claim 13 wherein the crude sorbic acid is contaminated by polymers and the aqueous solution comprises sodium acetate.

21. The process of claim 13 wherein the crude sorbic acid has a brown color and the aqueous solution comprises sodium acetate.

* * * * *